United States Patent [19]
Klein et al.

[11] Patent Number: 5,242,460
[45] Date of Patent: Sep. 7, 1993

[54] ATHERECTOMY CATHETER HAVING AXIALLY-DISPOSED CUTTING EDGE

[75] Inventors: Enrique J. Klein, Los Altos; Mark E. Plaia, San Carlos; James R. Kermode, Sunnyvale, all of Calif.; Donald S. Baim, Newton, Mass.; Richard P. Mueller, Mountain View, Calif.

[73] Assignee: Devices for Vascular Intervention, Inc., Redwood City, Calif.

[21] Appl. No.: 604,036

[22] Filed: Oct. 25, 1990

[51] Int. Cl.$^5$ ............................................. A61B 17/32
[52] U.S. Cl. .................................. 606/159; 606/170; 606/180; 604/22
[58] Field of Search ............... 604/22; 128/750, 751, 128/752, 753, 754, 755; 606/159, 170, 180

[56] References Cited

U.S. PATENT DOCUMENTS

| | | | |
|---|---|---|---|
| 3,320,957 | 5/1967 | Sokolik | 606/170 |
| 4,020,847 | 5/1977 | Clark, III . | |
| 4,627,436 | 12/1986 | Leckrone . | |
| 4,653,496 | 3/1987 | Bundy et al. . | |
| 4,669,469 | 6/1987 | Gifford, III et al. . | |
| 4,685,458 | 8/1987 | Leckrone . | |
| 4,745,919 | 5/1988 | Bundy et al. . | |
| 4,772,258 | 9/1988 | Marangoni et al. . | |
| 4,850,957 | 7/1989 | Summers | 604/22 |
| 4,857,046 | 8/1989 | Stevens et al. . | |
| 4,979,951 | 12/1990 | Simpson | 606/159 |
| 4,986,807 | 1/1991 | Farr | 604/22 |
| 5,074,841 | 12/1991 | Ademovic et al. | 606/170 |

FOREIGN PATENT DOCUMENTS

| | | | |
|---|---|---|---|
| 0163502 | 12/1985 | European Pat. Off. . | |
| 0373927 | 6/1990 | European Pat. Off. | 606/159 |
| 0665908 | 6/1979 | U.S.S.R. | 606/159 |

Primary Examiner—C. Fred Rosenbaum
Assistant Examiner—William Lewis
Attorney, Agent, or Firm—Townsend and Townsend Khourie and Crew

[57] ABSTRACT

Atherectomy catheters are described having a cylindrical cutting head rotatably mounted at the distal end of a catheter body. The head has an axially elongated aperture and an open interior. A severing means is disposed adjacent the elongated aperture such that atheromatous material invaginated by the head is severed and diverted into the interior of the head. A preferred embodiment has the elongated aperture helically-disposed about the central axis of the cylindrical head and a cutting means formed integrally along the periphery of the aperture. Another preferred embodiment has the cylindrical head provided with a tapered distal end that extends distally from a housing for the head and incorporates an extension of the elongated aperture.

55 Claims, 5 Drawing Sheets

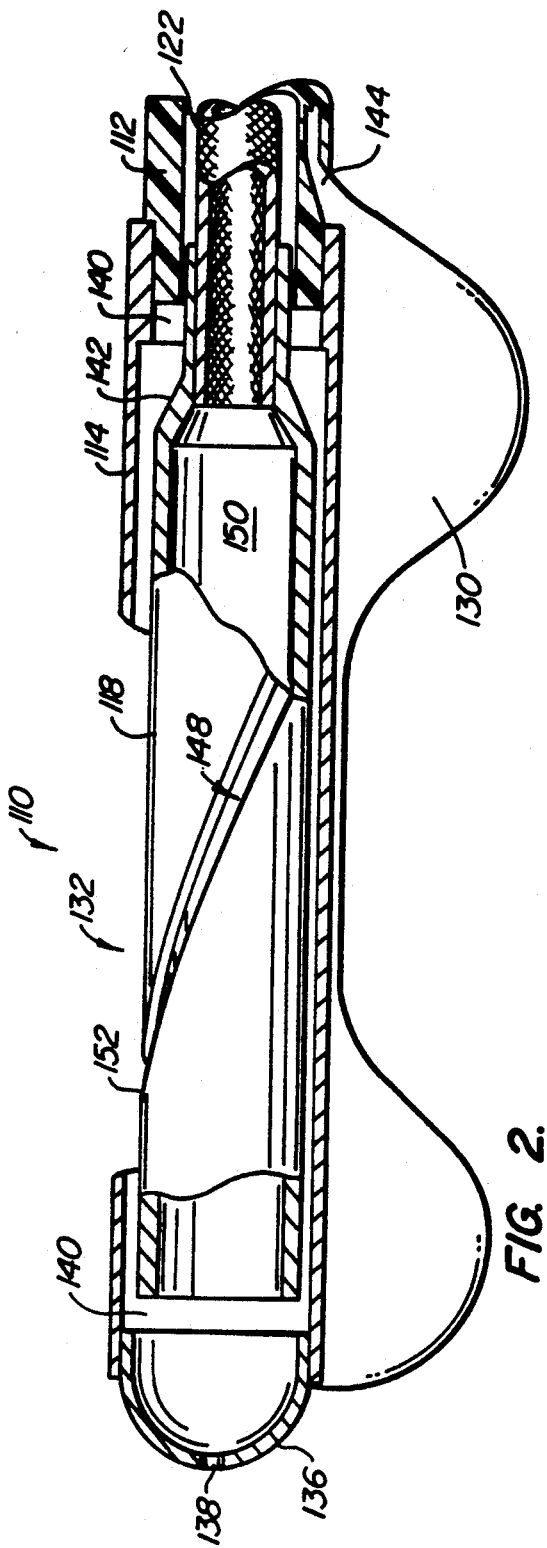
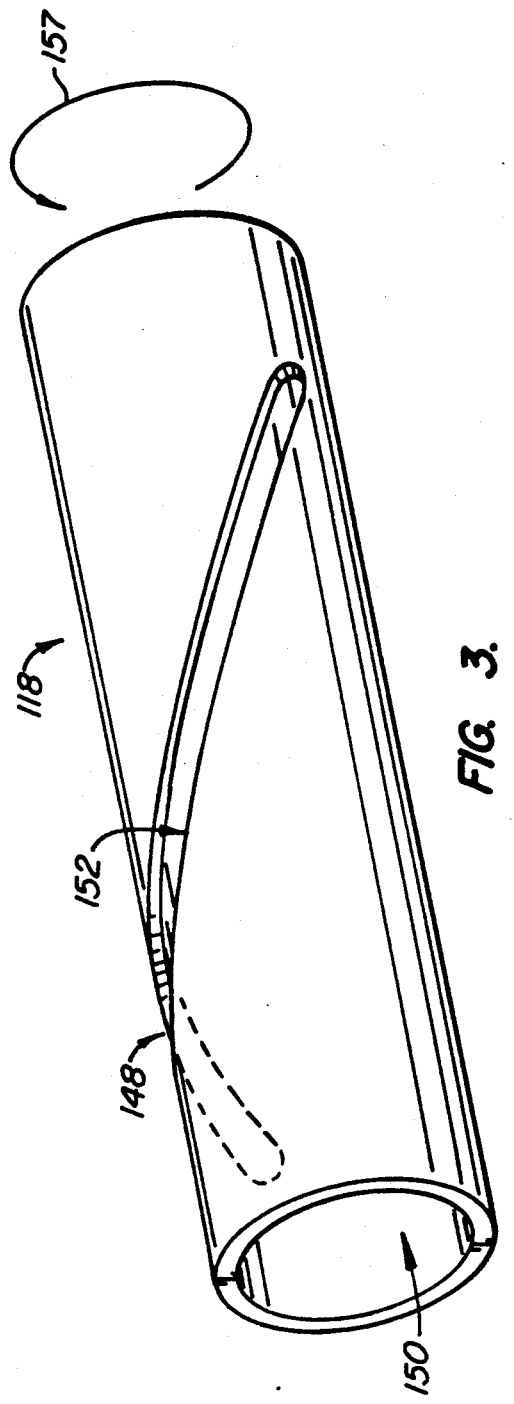

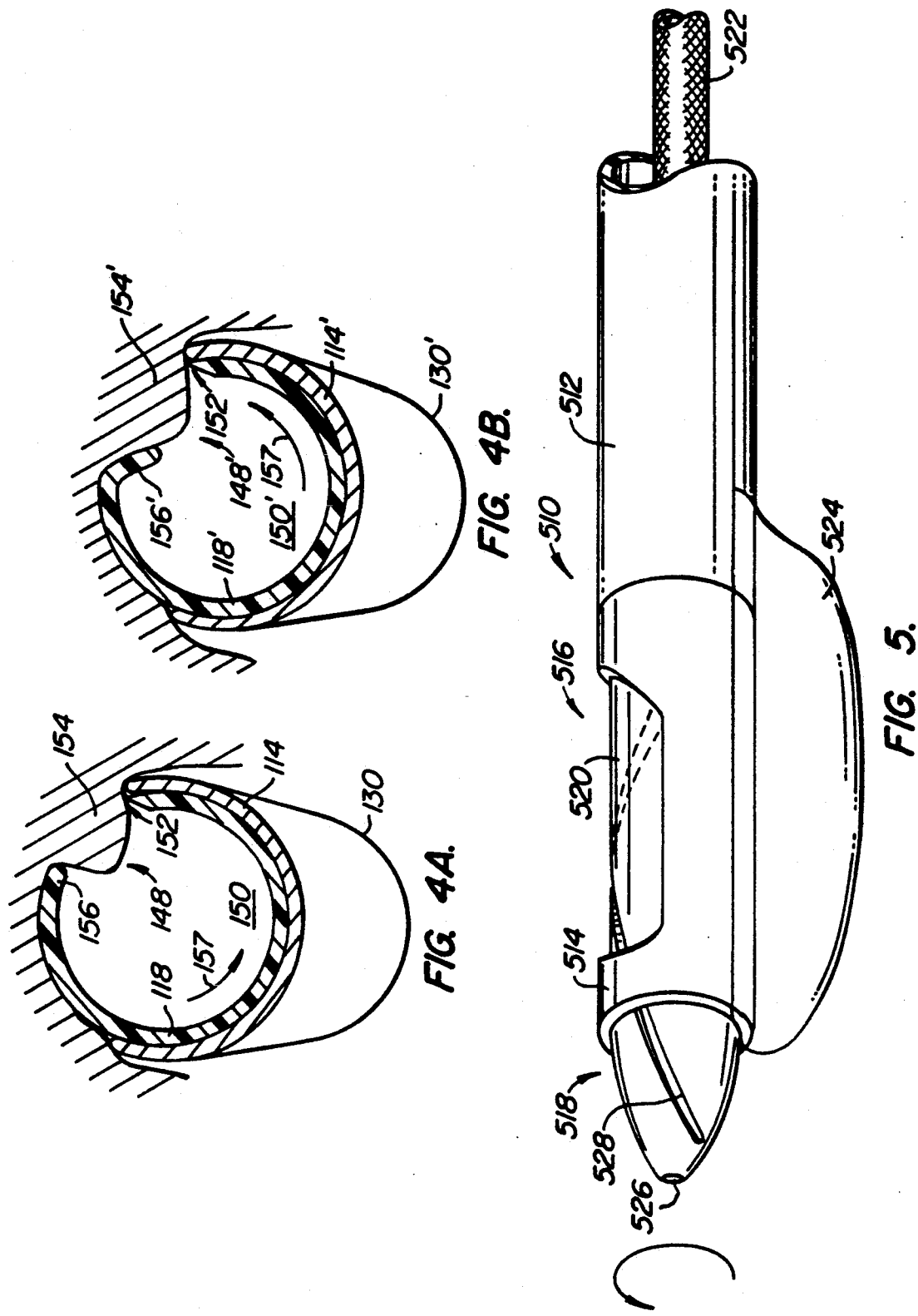

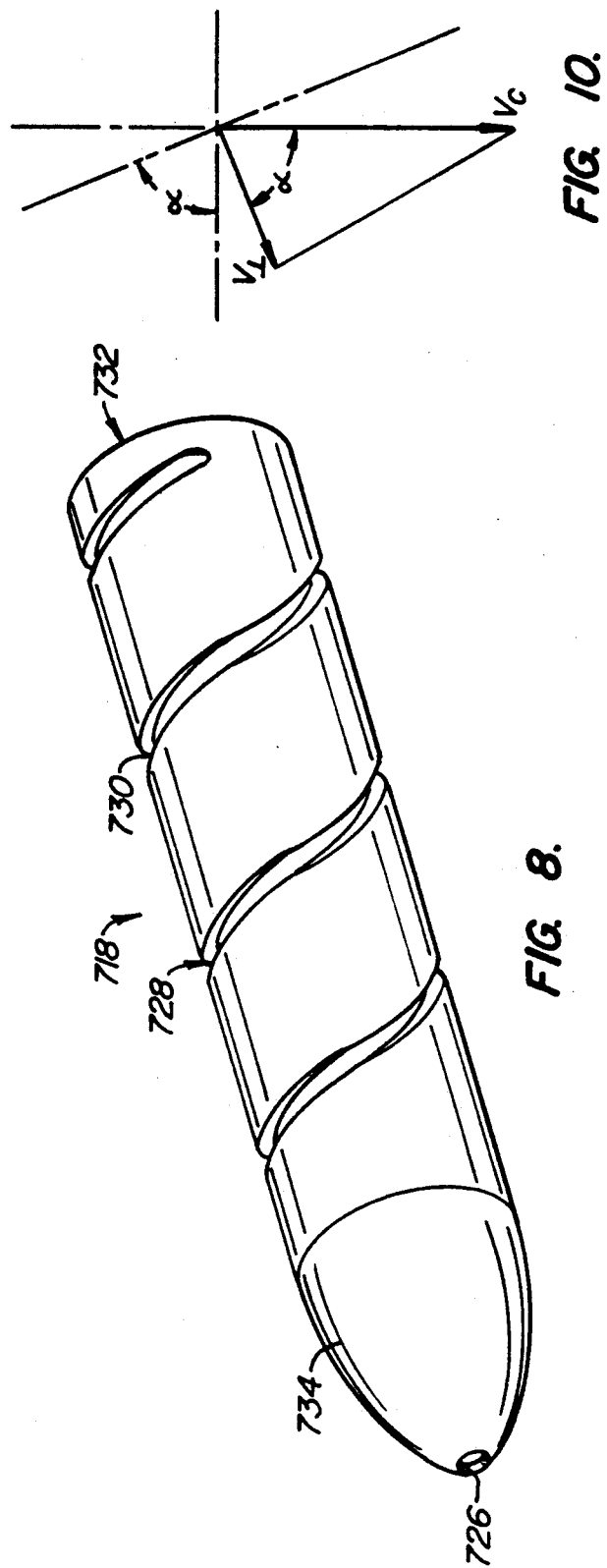
FIG. 8.
FIG. 9.
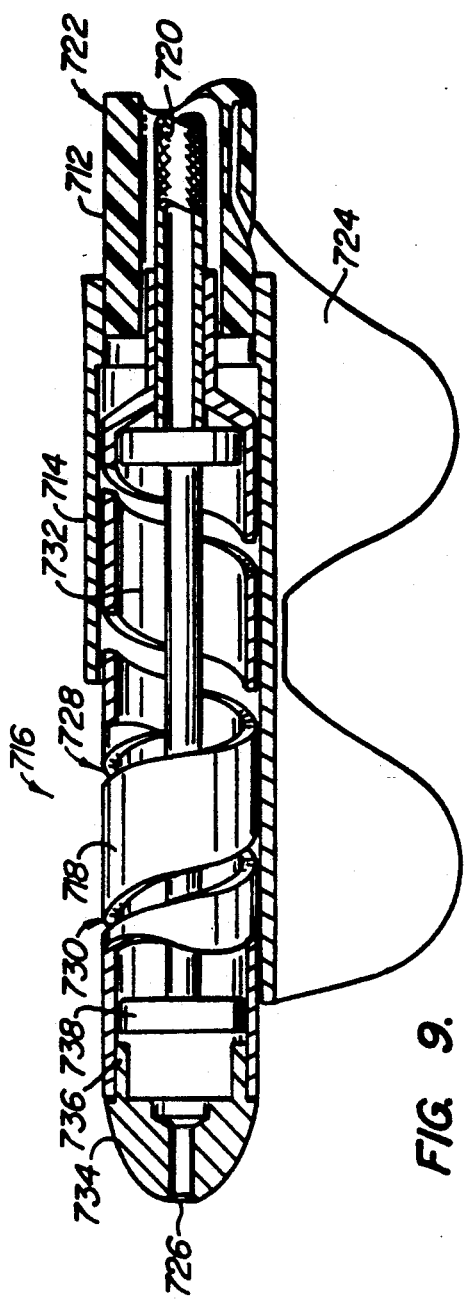
FIG. 10.

ATHERECTOMY CATHETER HAVING AXIALLY-DISPOSED CUTTING EDGE

CROSS-REFERENCE TO RELATED APPLICATIONS

The present application contains subject matter related to co-pending application Ser. No. 405,906, filed Sep. 12, 1989, which is incorporated herein by reference.

BACKGROUND OF THE INVENTION

1. Field of the Invention

The present invention relates generally to the construction and use of intravascular catheters. More particularly, the invention relates to atherectomy catheters having means at their distal ends for severing stenotic material.

Human vascular systems commonly become constricted, or stenotic, due to the accumulation of atheromatous material on the inner walls of the vascular lumens. When blood vessels such as arteries or vein grafts are involved, this condition is known as arteriosclerosis, or atherosclerosis. Atherosclerosis occurs naturally as a part of the aging process, but may also be aggravated by such factors as diet, hypertension and heredity. The intravascular deposits, or atheromas, tend to restrict blood flow causing ischemia, and in acute cases can result in myocardial infarction. The material properties of the deposits vary widely, with some deposits being relatively soft and others fibrous or calcified.

Many approaches for removing such deposits have been proposed. Generally, the approaches for removing atheromas have employed cutting, grinding or thermal ablation techniques. Of particular interest to the present invention are atherectomy devices and methods which employ a means for severing atheromatous material from the vessel wall.

In a typical atherectomy operation, a catheter having a suitable diameter is introduced into a lumen of the patient's vascular system and positioned adjacent the target material. A cutter blade provided at the distal end of the catheter is brought into contact with the target material. The catheter may either be a front-end cutting type or a side-cutting type. Front-end cutting atherectomy catheters are particularly useful in penetrating non-crossable lesions as they can "drill" through the lesion. Side-cutting atherectomy catheters are particularly useful in "debulking" a stenosed region and may employ an inflatable balloon disposed opposite the cutter blade to assist the blade in removing successive layers of stenotic material.

Although atherectomy catheters have enjoyed substantial success in treating vascular stenoses, some designs suffer from certain limitations. In particular, severing or abrading of the occluding material can result in the release of atheromatous particles which may then embolize the vasculature. Such emboli will lodge in the narrower regions of the vascular system and may significantly restrict the blood flow in critical regions of the vascular system, such as the coronary arteries. This may, in turn, endanger the patient's health.

Front-end cutting catheters are particularly prone to the release of large emboli into the vascular system. Some front-end cutting devices employ an exposed blade that severs or abrades the stenotic material. Usually provisions are made for aspirating the removed material, together with a substantial volume of blood, back through the catheter so that it is not released in vascular system. See, for example, U.S. Pat. Nos. 4,857,046, and 4,772,258. The use of aspiration with a rapidly rotating blade, however, cannot be relied on to capture all of the atheromatous material which is liberated during the atherectomy procedure.

Side-cutting catheters generally reduce the propensity for release of emboli into the vascular system since a housing is used to contain the blade and the housing is pressed firmly against the vessel wall having the atheromatous material. Most particles severed from the wall collect within the housing; more so than with front-end cutting catheters. See, for example, U.S. Pat. No. 4,669,469 and EPO Publication No. 0 163 502.

For these reasons, it is desired to provide atherectomy catheters that can remove stenotic material in a more controlled fashion with a minimum risk of releasing emboli into the vascular system. In particular, it is desired to invaginate atheromatous material within a substantially enclosed structure as the material is severed from the stenosed portion of the vascular lumen. Additionally, it is desired to provide a means for withdrawing the captured material from the enclosed structure. Also, it is desirable to provide methods for severing occluding material in such a manner as to ensure that it is retained within the means for containment until the catheter can be withdrawn from the patient. Finally, it would be desirable to provide atherectomy catheters which combine the ability of front-end cutters to penetrate lesions with the ability of side cutters to debulk stenosed regions.

2. Description of the Background Art

U.S. Pat. Nos. 4,857,046; 4,772,258; 4,745,919; and 4,653,496, all describe front-end cutting atherectomy catheters and the disclosure of each is incorporated herein by reference. Several of these patents further disclose use of a helical cutting blade to sever material from the vascular lumen. U.S. Pat. Nos. 4,685,458; 4,669,469; 4,627,436; and EPO Publication No. 0 163 502 each describe a side-cutting atherectomy catheter and the disclosure of each is incorporated herein by reference. These side-cutting devices may employ an inflatable balloon opposite an opening in the housing that contains the cutting blade. U.S. Pat. No. 4,020,847, describes a biopsy catheter having a slotted cylinder at its distal end, where the slot includes a cutting edge for severing tissue as the catheter is rotated.

SUMMARY OF THE INVENTION

According to the present invention, an atherectomy catheter comprises a catheter body having a cylindrical cutting head rotatably mounted at the distal end of the catheter body. The cylindrical cutting head has an open interior and at least one axially elongated aperture. A means for rotating the cylindrical head is provided within the catheter body, and a means for severing stenotic material and diverting said severed material into the interior of the head is disposed adjacent the elongated aperture. Thus, by rotating the cutting head, the catheter can sever atheromatous material which lies to the side of the catheter body and capture the severed material within the interior of the head.

A preferred embodiment of the invention employs a cylindrical cutting head having a tapered distal end. The axially elongated aperture and the severing means both extend to near the tapered distal end of the cylindrical cutting head, and the head thus is capable of forward-cutting through lesions blocking a vessel by axially advancing the catheter as the head is rotated. Usually, the cutting head may be axially advanced from the catheter body while the head is being rotated in order to facilitate penetration of severe occlusions. Alternatively, the entire catheter body may be advanced axially forward within the blood vessel lumen.

In a further preferred embodiment of the invention, the elongated aperture and severing means are helically disposed about a central axis of the head. The aperture and cutting means may have a relatively "shallow" helical angle so that the described helix subtends less than one complete turn about the cylindrical head, or may have a more steep angle so that the helix subtends one or more turns about the cylindrical head.

Both steep and shallow helical configurations will afford a more controlled removal of vascular atheromatous deposits than previously available devices because relatively thin "slices" will be removed from the vascular wall. However, cutting heads having relatively steep helical configuration will be generally more effective than shallow configurations in removing plaque from the vascular lumen as steep configurations provide a more aggressive cutting angle than shallow ones.

Also, both steep and shallow helical configurations will afford improved means for removing severed atheroma slices as the severed material will be contained within the interior of the cutting head. However, those embodiments employing relatively shallow configurations generally will be preferred with respect to withdrawing severed material since less open surface area is presented to the outside of the head by shallow apertures and since the apertures with such shallow angle cutting heads can be "shielded" by positioning the apertures adjacent the internal wall of housings. The selection of steep or shallow angle cutting catheters will depend on the particular application.

In a still further preferred embodiment of the invention, the severing means includes a cutting edge formed integrally along at least a part of the periphery of the elongated aperture, usually being formed along the edge of the aperture which trails as the head is rotated. The elongated aperture should allow substantial invagination of atheromatous material as the head is rotated. Such invagination can be enhanced by provision of an inwardly-inclined leading edge to the aperture.

The cylindrical cutting head may be mounted free of a housing. Usually, however, the head will be mounted within a housing at the distal end of the catheter, with the housing having an axially elongated opening through which the cylindrical cutting head is exposed. The axially elongated opening of the housing may be continued distally to expose the tapered distal end of the cylindrical cutting head. With such a configuration, the tapered distal end of the cutting head may be initially brought into contact with the stenotic material and used to "drill" through so that the housing can penetrate into even a severe occlusion. After the housing is located within the occlusion, the balloon can be used as described above to debulk the atheromatous material.

The present invention affords novel methods for removing atheromatous material from a patient's vascular system. The methods comprise the steps of introducing the distal end of the catheter into a vascular lumen adjacent the target material and rotating the cylindrical cutting head relative to the catheter body. The cutting head may be laterally displaced so that the atheromatous material is pushed into the aperture, severed by the severing means, and further captured within the interior of the head. Alternatively, the cutting head and/or the entire catheter may be axially advanced within the lumen of the vessel while the cutting head is being rotated so that a forwardly disposed portion of the severing means can penetrate a stenosis and remove the atheromatous material which lies in front of the catheter. Usually, the atheromatous material will be removed by sequentially advancing axially and then laterally displacing the cylindrical cutting head so that extended and otherwise impassable regions of stenosis can be penetrated and debulked. Optionally, the entire catheter body is rotated while the cutting head is being motor rotated and the inflation balloon is only moderately inflated in order to remove an extended arc of material within the blood vessel lumen. In all cases, the severed material can be removed from the vascular system by withdrawing the catheter with the material retained within the cylindrical cutting head.

The present invention thereby affords superior devices and methods for removing atheromatous material from a patient's vascular system. The vascular deposits can be controllably invaginated, severed and captured as relatively thin slices having a predetermined range of thickness, thereby reducing the risk of releasing particles that can embolize the vascular system. Severed atheromas will be largely retained within the cutting head until they can be withdrawn from the patient, thereby affording a means for withdrawing the material that does not require aspiration and the design complexities that accompany use of an aspiration means. Retention of severed atheromas will be particularly enhanced when a housing is employed with a side-cutting catheter so that the open aperture(s) of the cutting head will be adjacent either the internal wall of the housing or the vascular lumen during operation of the head. Also, the present catheters enable more straightforward techniques for debulking stenoses from nearly the entire region of a diseased vascular lumen by allowing the user to expand the scallop-shaped debulked region, normally produced by other catheters, using a "shaving" action until nearly all stenotic material is removed from the lumen.

BRIEF DESCRIPTION OF THE DRAWINGS

FIG. 2 is a broken-away view of the distal region of the catheter shown in FIG. 1.

FIG. 3 is a perspective view of the cylindrical cutting head of the catheter shown in FIG. 1.

FIG. 4A is a cross-sectional view taken along line 4A—4A of FIG. 1.

FIG. 4B is a cross-sectional view of an alternative embodiment of the cutting head of the present invention.

FIG. 5 is a perspective view of the distal region of a combined side and front-end cutting catheter constructed according to the principles of the present invention.

FIG. 8 is a perspective view of the cutting head of the catheter shown in FIG. 7.

FIG. 9 is a broken-away view of the distal end of the catheter shown in FIG. 7.

FIG. 10 is a vector diagram showing the dependence of cutting edge velocity on the angle defined by the aperture pitch and the central axis of the cutting head.

DETAILED DESCRIPTION OF THE PREFERRED EMBODIMENTS

The intravascular catheters of the present invention will have an elongated catheter body having distal and proximal ends. The catheters will comprise a cylindrical cutting head for removing atheromatous material at the distal end of the catheter body. The cylindrical cutting head will be rotatably mounted at the distal end of the catheter body. Also, the cylindrical head will have an open interior and at least one axially elongated aperture. Means will be provided within the catheter body for rotating the cylindrical head. Additionally, means for severing atheromatous material will be disposed adjacent elongated aperture(s) of the cylindrical head so as to divert severed material into the interior of the head.

In a preferred embodiment, the cylindrical head will have a tapered distal end. The tapered end may be formed integrally with the cylindrical body of the head or, alternatively, may be formed separately as a "nosepiece" attached to the distal end of the cylindrical head. The axially elongated aperture of the head may extend continuously into the tapered region of the head to afford front-end cutting capability. Alternatively, the tapered distal region of the head may include a separately formed aperture having an adjacent severing means like that provided on the cylindrical head. Whenever a nosepiece is provided on the distal end of the head, the nosepiece preferably will be detachable from the cylindrical body of the head to permit removal of severed material within the head. It is especially desirable that the nosepiece be detachable when the nosepiece does not include a severing means, in order to allow cleaning of the interior of the head. Typically, the distal tip of the head will be provided with an orifice to permit passage of a guidewire therethrough.

The catheters of the present invention will usually be provided with a housing for the cylindrical cutting head at the distal end of the catheter. Such a housing will have an axially elongated opening through which target atheromatous material can contact the severing means of the rotatable head. Preferably, an inflatable balloon will be provided external the housing and generally opposite the axially elongated opening, with the balloon facilitating intimate contact of the rotatable head with the vascular lumen and atheromatous material.

Atheromatous materials that can be removed by the present devices include all naturally-occurring occlusions found in vascular lumens, e.g., lipoprotein deposits, blood clots, atherosclerotic plaques, and the like. The materials may be hardened plaques or relatively soft atheromas, with the present invention particularly suited for removing relatively soft deposits.

A. Catheter Bodies

Figure 1:
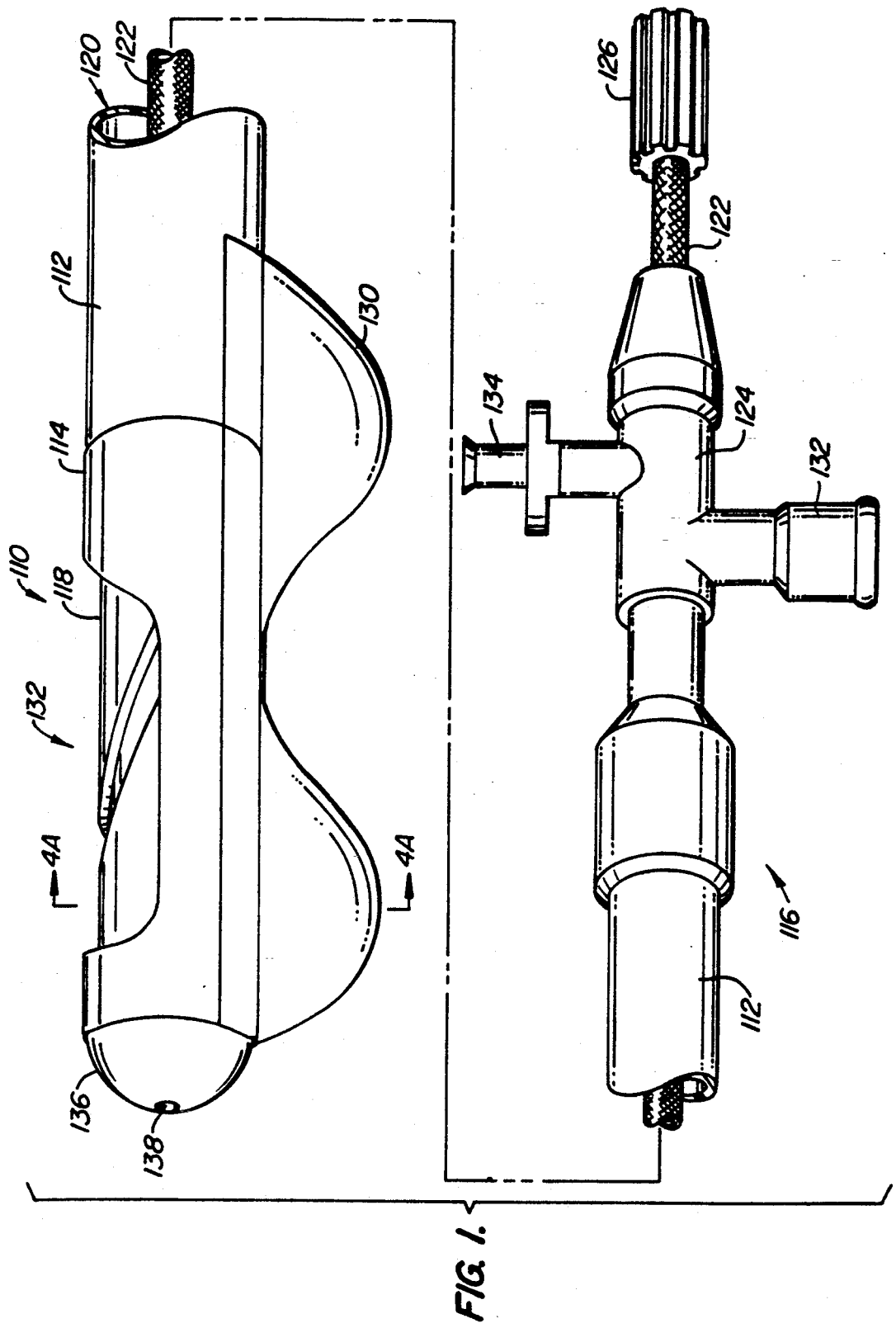
FIG. 1 is a side view of a side-cutting atherectomy catheter constructed in accordance with the principles of the present invention.

Referring now to FIG. 1, an atherectomy catheter 110 constructed in accordance with the principles of the present invention comprises a catheter body 112, a cylindrical housing 114 attached to the distal end of catheter body 112, and a connector manifold 116 attached to the proximal end of the catheter body. A cylindrical cutting head 118 is disposed within the interior of housing 114.

As illustrated, the catheter body 112 includes an annular lumen 120 which extends through the entire length of the catheter body. Lumen 120 allows passage of torque cable 122 therethrough. Torque cable 122 is typically a braided cable or the like and is attached to the proximal end of rotatable cutting head 118. Methods for constructing suitable braided structures for torque cable 122 are described in U.S. Pat. Nos. 4,425,919; 3,924,632; and 3,485,234, the disclosures of which are incorporated herein by reference. Torque cable 122 passes through manifold housing 124 and is secured at its distal end to drive spindle 126. Drive spindle 126 is adapted to be connected to a motor drive unit of the type described in U.S. Pat. No. 4,771,774, the disclosure of which is incorporated herein by reference.

The atherectomy catheter 110 will usually be adapted to rotate cutting head 118 relative to catheter 110 to effectively cut atheromatous tissue with the catheter 110 motionless within the vessel. Alternatively, cutting over an extended arc of the inner lumen wall can be achieved by manually rotating the entire catheter body 12 while the cutting head 118 is being rotated at a relatively high rotational rate by the motor drive.

An inflatable balloon 130 is formed on the outside of housing 114 and disposed generally opposite to the location of an elongate aperture 132 formed in a side of housing 114. The interior of balloon 130 is in fluid communication with inflation port 132 provided on manifold housing 124 to allow inflation of the balloon. A second port 134 is provided on housing 124 to allow perfusion of fluids through annular lumen 120 of catheter body 112.

Catheter body 112 will generally be a flexible tube having at least one lumen of the type generally employed in vascular catheters. Suitable materials and methods for forming such flexible catheter body tubes are described in U.S. Pat. No. 4,669,469, previously incorporated herein by reference. The catheter bodies will be comprised of a flexible material so as to minimize the rigidity of the catheter, especially when atheromatous material is to be removed from the tortuous paths of coronary arteries.

A tapered endpiece 136 is attached to the distal end of housing 114, which provides a means for sealing the distal end of housing 114 as well as means for tapering the distal end of housing 114 so that narrow passages in a vascular lumen can be more easily penetrated. Endpiece 136 includes an orifice 138, which allows passage of a moveable guidewire therethrough.

The above-described catheter represents only one embodiment of the present invention and may be modified in view of the remaining disclosure herein. For example, the dual-lobed balloon 130 could be substituted with a single-lobed balloon or with two single-lobed balloons. Additionally, endpiece 136 can have any shape consistent with effective use of the catheter, e.g., conical, dome-shaped, and the like. Also, endpiece 136 may be dispensed with altogether and the housing 114 substituted with a housing having a continuous seal about its distal end. Other modifications would be readily apparent to a skilled practitioner.

Referring now to FIG. 2, a side view of catheter 110 is depicted with portions broken away to reveal the interior of the catheter. Thus, catheter body 112 is attached at its distal end to housing 114 having open interior 140. Interior 140 contains cutting head 118 which is attached at its proximal end to torque cable 122 via shank 142. Torque cable 122 extends proximally through annular lumen 120 provided in catheter body 112.

Opposite elongated aperture 132 in housing 114 is balloon 130 which is connected at its proximal end to an inflation lumen 144. Inflation lumen 144 connects the interior of balloon 130 to an inflation port. The inflation lumen may be provided integrally within the catheter body. Usually, however, the inflation lumen will be defined, as shown in FIG. 2, by an outer sheath 146 formed over catheter body 112. The fabrication of such coaxial inflation lumens is described in U.S. Pat. No. 4,411,055, the disclosure of which is incorporated herein by reference.

B. Cylindrical Cutting Heads

The instant atherectomy catheters will be provided with a cutting head rotatably mounted at the distal end of the catheters. The cutting head may be mounted free of any housing for containing the cutting head. Optionally, and preferably, however, the cutting head will be contained within a housing at the distal end of the catheter. When a housing is employed to support the cutting head, the head will be exposed to target atheromatous material through an axially elongated opening in the housing wall.

Referring to FIGS. 2 and 3, the interior 140 of housing 114 contains cylindrical cutting head 118. Head 118 includes an axially elongated aperture 148 helically disposed about the central axis of the head. The elongated aperture 148 allows invagination of atheromatous material into the interior 150 of cutting head 118. Helical aperture 148 subtends less than one half of a complete turn about the central axis of cylindrical head 118. When the aperture 148 in head 118, as illustrated, subtends less than approximately one half turn about the head's surface, and the elongated aperture 132 in housing 114 also subtends less than approximately one half turn about the housing surface, then head 118 can be positioned so as to shield aperture 148 wholly within housing 114. Such positioning will help to avoid unintended nicking and cutting of the vascular wall while the catheter is being introduced through the vascular lumen and will prevent release of atheroma particles from the interior 150 of head 118 during withdrawal of the head from the vascular system.

Cutting head 118 further includes a cutting edge 152 formed along a portion of the periphery of aperture 148. Preferably, cutting edge 152 extends along the distal side of aperture 148 so that a distal thrust is exerted on torque cable 122 as the head 118 is rotated in the direction of arrow 157. The distal thrust is absorbed by endpiece 136 which is fixedly attached to housing 114. Cutting edge 152 severs atheromatous material 154 which penetrates into the aperture 148, as illustrated in FIG. 4A. The severed atheromatous material is simultaneously diverted by cutting edge 152 into the interior 150 of head 118.

In a typical application, cutting head 118 will be positioned adjacent such atheromatous material as illustrated by atheroma 154. Housing 114 will be made to press against the vascular lumen so as to contact atheroma 154 with cutting head 118 contained within housing 114. When aperture 148 is aligned with atheroma 154 the atheroma will tend to penetrate the aperture and thereby to be invaginated by head 118. Balloon 130 can further assist in invaginating atheroma 154 by pressing against the opposite wall of the vascular lumen and thus further urging aperture 148 against the exposed vessel surface. Balloon 130 will also help to stabilize housing 114 within the lumen as cutting head 118 is manipulated by the interventionist. As head 118 is rotated relative to the catheter, atheroma 154 will be compressed briefly against the intima wall by edge 156. As cutting head 118 further rotates in the direction of the arrow 157, atheromatous material sliding past edge 156 will be released from compression and will penetrate aperture 148. The atheromatous material, thus invaginated by cutting head 118, is readied for severance from the vessel wall by cutting edge 152. Cutting edge 152 will engage atheroma 154 at a point coincident with the periphery of aperture 148 and will sever and divert atheroma 154 into the interior 150 of head 118.

An alternative embodiment for a cylindrical cutting head is shown in FIG. 4B. Parts corresponding to those described for FIG. 4A are presented with primed reference numerals. Thus, cutting head 118' includes a cutting edge 152' which severs and diverts atheroma 154' into the interior 150' of head 118'. Invagination of atheroma 154' within cutting head 118' through aperture 148' is assisted by lip 156' which is radially inclined inward toward the interior 150' of head 118' along a portion of the edge of aperture 148'. The angle of inclination of the edge is not critical and can be any value that generally aids in invaginating atheromatous material. Typically, the angle of inclination of the lip from the tangent to the head at the juncture of the lip with the head will be in the range of 10°–15°.

C. Combined Side and Front-end Cutting Heads

Referring now to FIG. 5, the distal region of a combined side and front-end cutting catheter 510 constructed in accordance with the principles of the present invention is depicted. Catheter 510 comprises a catheter body 512 attached at its distal end to housing 514. Catheter body 512 has essentially the same dimensions and is constructed from the same materials as the catheter bodies described above. Housing 514 is provided with axially elongated opening 516 in its side and with distal opening 518 at its distal end. The openings permit access to atheromatous material located either laterally or ahead of the distal end of catheter 510.

Cylindrical cutting head 520 is rotatably mounted within housing 514. Rotatable head 520 is attached at its proximal end to torque cable 522 which extends proximally to a point external the patient's body. Opposite the side opening 516 in housing 514 is an inflatable balloon 524 which will assist upon inflation in pressing cutting head 520 against atheromatous material on the vascular lumen. Additionally, head 520 has an orifice 526 which permits the passage of a movable guidewire therethrough. The torque cable 522 will include a lumen that permits such a guidewire to pass proximally through the catheter.

Catheter 510 will include a connector manifold (not illustrated) which is generally the same as connector manifold 116 in FIG. 1, except that a lever (not illustrated) for axially advancing the torque cable 522 will be provided. The construction and use of axial advance levers in catheters having torque cables is well described in U.S. Pat. Nos. 4,669,469 and 4,771,774, the disclosures of which have previously been incorporated herein by reference. The advance lever in catheter 510 can be used to advance the distal end of cutting head 518 from the forward end of housing 514 while the head is being rotated with a motor drive, as described above. In this way, the tapered distal end of the cutting head 518 can penetrate even severe occlusions by "drilling" into narrow lumens which would otherwise be impassable.

Figure 6:
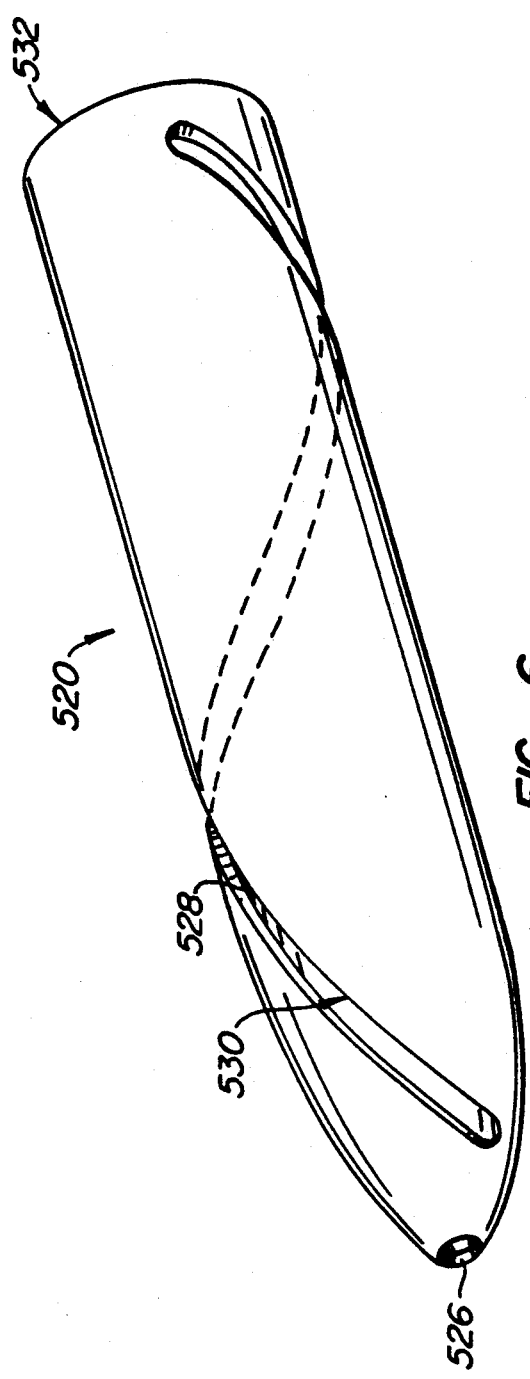
FIG. 6 is a perspective view of the cutting head of the catheter shown in FIG. 5.

As illustrated in FIGS. 5 and 6, cylindrical head 520 is tapered at its distal end with the tapered distal end extending out from the distal end of housing 514. The tapered distal end of head 520 is formed continuously with the cylindrical region of head 520 to give an integrated rotatable cutting member. Alternatively, the distal tapered end of the cutting head may be provided as a separately formed member that is subsequently attached, either permanently or detachably, to the cylindrical region of the head.

Cylindrical head 520 has a helically disposed axially elongated aperture 528 that extends from the cylindrical region of head 520 to near the tapered distal end of the head. A cutting edge 530 is formed integrally with the body of head 520 along the proximal edge of aperture 528. Also, cutting head 520 has an open interior 532 to which severed atheromas are diverted after being severed from the lumen wall.

Figure 7:
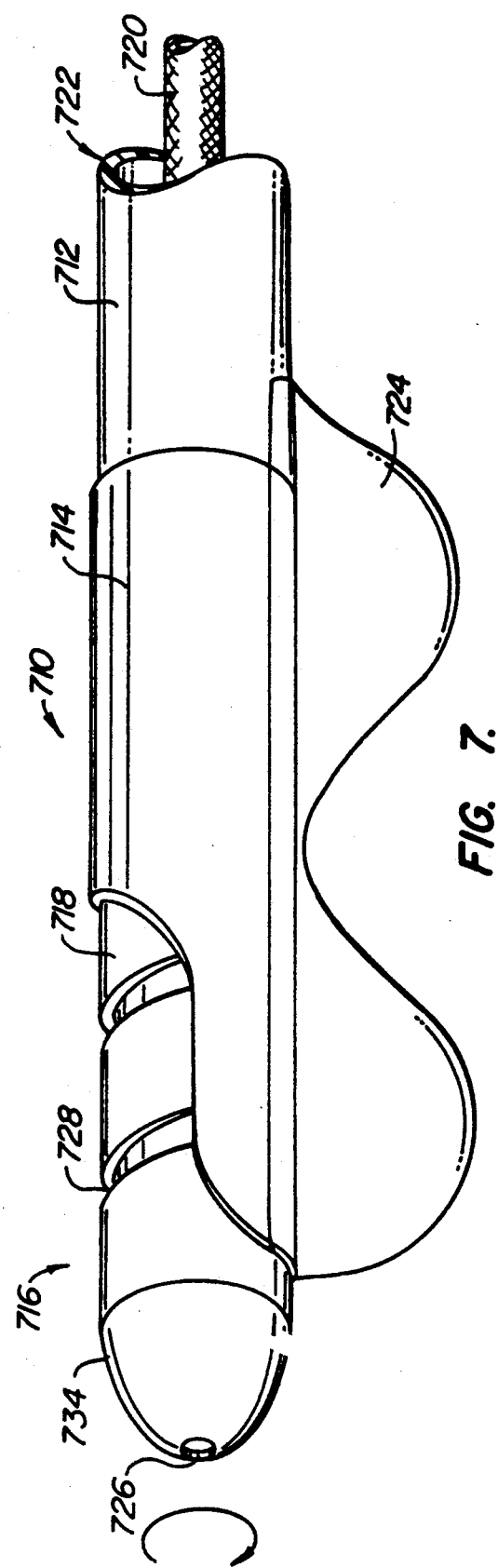
FIG. 7 is a perspective view of an alternative embodiment for a side-cutting catheter constructed in accordance with the principles of the present invention.

Referring now to FIG. 7, another preferred embodiment of a combined side and front-end cutting catheter is depicted. Thus, atherectomy catheter 710 includes catheter body 712 attached at its distal end to housing 714, which has an axially elongated opening 716 in its side wall and distal end. Elongated opening 716 extends distally from a first point along the side of housing 714 to a second point on the opposite side of the housing which is located distally from the first point. Opening 716 is formed as an unbroken open section of housing 714, i.e., the periphery of the opening forms a continuous and complete loop to form opening 716.

Cylindrical cutting head 718 is rotatably mounted within housing 714 and extends distally from housing 714 through opening 716. The proximal end of head 718 is attached to torque cable 720 which extends through lumen 722 of catheter body 712. Inflatable balloon 724 is provided opposite opening 716 in order to assist in urging cutting head 718 into contact with target atheromas. Cutting head 718 has orifice 726 provided for the passages of a guidewire.

Referring now to FIG. 8, a more complete cutting head 718 is shown. Head 718 will typically be comprised of a strong, biologically compatible metal, e.g., stainless steel. The thickness of the metal sheet comprising head 718 will usually be about 0.004 inches. Cylindrical head 718 further has a helically disposed aperture 728 about the central longitudinal axis of head 718. As illustrated, the helical aperture 728 subtends more than one complete turn about cutting head 716. The width of aperture 728 may vary substantially, depending upon the particular use contemplated for the catheter; however, a width of about 0.030 inches for the aperture will be typical.

A cutting edge 730 is provided along the proximal edge of aperture 728. Cutting edge 730 severs atheromatous material and diverts it to the interior 732 of head 718 until it can be conveniently withdrawn from the vascular lumen together with the catheter. A tapered endpiece 734 is provided at the distal end of cutting head 718 in order to assist in penetrating lesions and in finding the desired course through the vascular system.

Referring now to FIG. 9, the interior of the catheter shown in FIG. 7 is shown. Thus, housing 714 is attached to the distal end of catheter body 712 and has an axially elongated opening 716 through which cutting head 718 extends distally. The cylindrical head 718 is mounted to the distal end of torque cable 720 as described for a previous embodiment. The torque cable extends proximally through lumen 722 provided in body 712. Inflatable balloon 724 is positioned opposite elongated opening 716 and is inflated via an inflation lumen as described for a previous embodiment. Orifice 726 in the distal end of head 718 allows passage of a guidewire, which extends proximally through a lumen provided in torque cable 720.

Axially elongated aperture 728 in cutting head 718 subtends more than one complete turn about cylindrical head 718 and allows invagination of atheromatous material by head 718 so that cutting edge 730 can sever and divert such material to the interior 732 of head 718. Tapered endpiece 734 including orifice 726 is detachably fit via tabs 736 into the distal end of cutting head 718. Endpiece 734 is detachable from the distal end of head 718 so that the interior 732 of cutting head 718 can be exposed. Clean-out spool 738 is slidably disposed within the interior of cylindrical cutting head 718 and provides a means for withdrawing severed atheromatous material from the interior 732 and through the forward distal end of head 718. Alternative means for attaching the endpiece to the cutting head will be readily apparent to the skilled practitioner as will alternative designs for the spool located internal the cutting head.

A still further preferred embodiment of the present invention will have the detachable endpiece and clean-out spool provided as a unitary component of the cutting head, which will permit the spool to be withdrawn distally from the interior of the head together with the distal endpiece. Such a component may be discarded with any atheromas withdrawn with the component.

D. Further Considerations

The axially elongated apertures of the cutting heads of the present invention may be disposed in a non-helical fashion about the cutting head. For example, the elongated aperture may be disposed essentially collinearly with the central axis of the cylindrical cutting head.

Preferably, however, the elongate apertures will be helically disposed about the cylindrical cutting head so that rotation of the head causes a first velocity component normal to and a second velocity component parallel to the edge of the helix to enhance the resultant cutting action. The direction which the cutting head is rotated will depend on the direction of the helix (i.e., right-hand or left-hand) and on whether the distal side or proximal side of the aperture is sharpened to define the cutting edge. For the embodiment of FIGS. 1-3, the aperture 148 is a right-hand helix with the distal side of the aperture being sharpened. Rotation in the direction of arrow 157 (counter-clockwise when viewed distal to proximal) will cause the sharpened edge 152 to cut into atheroma while the cutting head 118 experiences a distal thrust. The same result could be achieved with a left-hand helical aperture by rotating the cutting head in the opposite (clockwise) direction. So long as the distal side of the aperture carries the cutting edge, the cutting head will experience a distal thrust when rotated in the appropriate cutting direction. Such a distal thrust is desirable since it is absorbed by the endpiece and allows cable 122 to operate as a torsional member without experiencing tension or compression during use of the cutting head 118.

For the embodiments of FIGS. 5-9, the cutter torque cable 522, 720 will necessarily be under compression as the cutting head 520, 718 is advanced forward through the atheromatous material or is used in the side-cutting mode. Thus, effective cutting will be achieved by having the cutting edge on the proximal side of the cutting aperture and rotating the cutting head in the direction dictated by the helical direction, i.e., counter-clockwise when viewed distal to proximal for left-hand helices (as illustrated in FIGS. 5 and 6) and clockwise for right-hand helices (as shown in FIGS. 7-9).

In some applications, a plurality of helices about the rotatable head may be preferred. Of course, the elongated aperture of the instant cutting heads may be disposed in a combined helical and non-helical fashion about the central axis of the head as well, if such a configuration is desired.

When a cutting edge is employed as the severing means of the present invention, such cutting edge may be formed as a smooth edge along the elongated aperture of the cutting head. Alternatively, the cutting edge may be serrated, especially when hardened plaques are expected to be encountered within the vascular lumen.

As depicted in FIG. 10, the effective cutting velocity of the severing means adjacent a helical aperture will generally be less than the rotational velocity of the cylindrical cutting head. Thus, when a helical aperture forms an angle $\alpha$ with the central axis of the cutting head, the velocity vector $V_\perp$ normal to the aperture is displaced relative to the rotational velocity vector $V_c$ by the same angle $\alpha$. The cutting velocity $V_\perp$ of the severing means, will therefore be less than $V_c$ and as given by the equation:

$$V_\perp = V_c \cdot \cos \alpha.$$

Generally, cutting heads having a small value for $\alpha$, i.e., shallow helix heads, will be more effective at retaining severed or abraded material within the cutting head than will steep helix cutting heads, which have relatively large values for $\alpha$. However, steep helix cutting heads will be more effective than the shallow helix cutting heads at slicing atheromatous material from the stenotic vessel lumen.

E. Housings

The distal ends of the catheters illustrated above are fitted with a cylindrical housing for the cylindrical cutting head inside. The internal diameter of the cylindrical housing will be large enough to accommodate the head within but small enough so that the housing fits around the head sufficiently closely to prevent undesired motions of the head, such as wobbling during rotation, as well as to prevent the release of atheroma particles from the cavity within the cutting head. Typically, the housing will have an outside diameter close to that for the catheter body, i.e., 5 to 7 French for coronary arteries and 7 to 11 French for peripheral arteries.

The cylindrical housings of the present invention will be sufficiently small to allow the catheter to "snake" through the tortuous paths of the vascular system. However, the housings should also be large enough to allow as much atheromatous material as possible to be severed and captured without the necessity of removing the catheter from the patient for cleaning purposes prior to relocating the housing to the same or a different cutting site in the vascular lumen. Typically, in the configurations of FIGS. 1, 2, and 5, the housing will have an axially elongated opening, or window, through which atheromatous material will contact the cutting head, which is about 10 mm in length.

The housings employed with the present invention may be flexible housings of the type described in U.S. Pat. No. 4,781,186, the disclosure of which is incorporated herein by reference. Flexible housings may also be provided by other designs, including laminate constructions having a plurality of overlapping slotted housings where the slots are formed in a offset pattern, i.e., the slots in one layer are covered by the material of another layer. The slotted layers can be formed from machined metals, such as stainless steel, which may be further thinned by chemical etching. Other suitable materials include thermosetting plastics and thermoplastics, e.g., urethanes, polyvinyl chlorides, nylons, etc.

Flexible housings may also be machined to form a series of slots which penetrate the cylindrical wall of the housing from opposite sides of the elongate aperture. The slots form independent segments in the housing and provide the desired flexibility without loss of circumferential stiffness. Optionally, the segmented housing may be coated in a plastic material to enclose the interior without a substantial loss of flexibility. The flexible housing may also be formed as laminates of relatively thin, flexible layers which accommodate bending as the successive layers slide over one another. Suitable constructions of the flexible housing are presented in U.S. application Ser. No. 405,906, which is incorporated herein by reference.

E. Method of Use

As will be apparent from the above discussion, novel methods for removing atheromatous material from vascular lumens are provided by the present invention. Thus, the distal end of a catheter is introduced into the lumen and positioned adjacent the target atheromatous material. The cylindrical cutting head mounted at the distal end of the catheter will be rotated so that material invaginated by the cutting head will be severed and diverted into the interior of the head. The catheter will be withdrawn from the vascular lumen with the severed material remaining within the cylindrical head.

The catheter of the present invention may be utilized in a variety of operating modes, depending in part on the particular embodiment which is employed. The embodiment of FIG. 1 is intended primarily for side-cutting where the balloon 130 is inflated to laterally engage the cutting head 118 against atheromatous material while the housing 114 remains otherwise stationary within the blood vessel. The cutting head 118 is then rotated using a motor drive (while the catheter 110 remains substantially stationary) to sever and remove the atheromatous material. Alternatively, the entire catheter 110 can be manually rotated (while the balloon is inflated at a moderate pressure and the cutting head is rotated by the motor drive) in order to sever atheromatous material from an extended portion of the lumen arc.

The catheter 510 of FIG. 5 can be operated in a side cutting mode similar to that of FIG. 1, or can be operated in a front-cutting mode by rotating the cutting head 520 and moving the head axially forward within the blood vessel so that the tapered end of the cutting head can penetrate the atheromatous material. Usually, the cutting head 520 will be extended axially forward from the housing 514 by advancing the torque cable 522 in the distal direction, typically using an advance lever (not shown) of the type described in U.S. Pat. No. 4,669,469, previously incorporated herein by reference, with the balloon 524 fully inflated to anchor the housing. Alternatively, the entire catheter 510 may be advanced through the blood vessel, with the balloon 524 deflated or inflated with moderate pressure, in which case no advance lever is required (although it may be present). It would also be possible to manually rotate the entire catheter 510 while the cutting head 520 is being motor rotated to effect severing of the atheromatous material over an extended portion of the lumen arc.

Use of catheter 710 (FIGS. 7–9) is similar to that of catheter 510, with two differences. First, the steep helical angle ($\alpha$) of aperture 728 will be more effective in removing atheromatous material and is preferred when hardened stenotic material is being removed. Second, the elongated opening 716 in housing 714 exposes a continuous length of the cutter head 718 from the distal tip rearward, while protecting the opposite side of the vessel from the cutting edge. Such a configuration is useful for directional cutting when advancing the catheter 710 while rotating the cutting head 718 and inflating balloon 724 with a moderate pressure.

It will be appreciated, of course, that the cutting head 520 (FIG. 6) could be substituted for cutting head 718 in housing 714 of catheter 710. In this way, directional cutting, as just described, could be achieved with a less steep helical angle.

The size, shape and thickness of the atheroma particles severed from the vascular wall will depend on the type of atheroma encountered by the device, but will also be impacted by the features and operating parameters of the atherectomy catheter of the present invention. For example, the rotational velocity of the head, the width of the aperture, the angle of inclination of the inwardly-inclined edge, the helical pitch of the aperture, and the like, each will affect the size, shape and thickness of particles severed from the lumen wall. These parameters may be varied so as to obtain the desired particle size, shape and thickness for a particular application.

Also, whenever a housing is employed and the head has an axially elongated aperture disposed so that the aperture subtends less than one half of a turn around the central axis of the cutting head, the aperture may be rotationally positioned substantially opposite the elongated opening of the housing prior to introducing or withdrawing the head from the vascular lumen. In this way, severed material internal to the head can be prevented from escaping the interior of the head until the catheter can be withdrawn. Also, the interior of the vascular lumen can thereby be shielded from the sharp cutting edges of the cylindrical head until the head is positioned adjacent target atheromas.

Although the foregoing invention has been described in detail for purposes of clarity and understanding, it will be obvious that certain modifications may be practiced within the scope of the appended claims.

What is claimed is:

1. An atherectomy catheter comprising:
    a catheter body having a proximal end and a distal end;
    a cylindrical cutting head rotatably mounted at the distal end of the catheter body, said cylindrical head having a cylindrical wall surrounding an open interior and an axially elongated aperture in said wall, said wall having a surface area excluding said aperture which is substantially greater than the area defined by said aperture, said aperture being helically disposed about a central axis of the cylindrical cutting head and subtending less than a complete turn thereabout;
    means within the catheter body for rotating the cylindrical head; and
    means disposed adjacent the elongated aperture of the cylindrical head for severing atheromatous material and diverting severed material into the interior of said head as the head is rotated.

2. A catheter as in claim 1, wherein the cylindrical cutting head is tapered at its distal end and wherein said tapered distal end extends out from the distal end of the catheter body.

3. A catheter as in claim 2, wherein the axially elongated aperture extends to near the tapered distal end of the head.

4. A catheter as in claim 1, wherein the means for severing and diverting comprises a cutting edge which forms at least a portion of a trailing edge of the aperture as the cylindrical cutting head is rotated.

5. A catheter as in claim 4, wherein the means for severing and diverting further comprises a lip which is inclined radially inward along at least a portion of a leading edge of the aperture.

6. An atherectomy catheter comprising:
    a catheter body having a proximal end and a distal end;
    a housing attached to the distal end of the catheter body, said housing having a single axially-aligned elongated opening;
    a cylindrical cutting head rotatably mounted in the housing, said head having a cylindrical wall surrounding an open interior and an axially elongated aperture in said wall, said wall having a surface area excluding said aperture which is substantially greater than the area defined by said aperture;
    means within the catheter body for rotating the cylindrical head;
    means disposed adjacent the elongated aperture of the cylindrical head for severing atheromatous material and diverting severed material into the interior of said head as the head is rotated; and
    means on the housing of urging the housing in the direction of the opening when the catheter is in a blood vessel.

7. A catheter as in claim 6, wherein the urging means comprises an inflatable balloon mounted externally on the housing and disposed generally opposite the elongated opening.

8. A catheter as in claim 6, wherein the cylindrical cutting head is tapered at its distal end and wherein said tapered distal end extends out from an opening in the distal end of the housing.

9. A catheter as in claim 8, wherein the axially elongated aperture extends to near the tapered distal end of the head.

10. A catheter as in claim 6, wherein the means for severing and diverting comprises a cutting edge which forms at least a portion of a trailing edge of the aperture as the cylindrical cutting head is rotated.

11. A catheter as in claim 10, wherein the means for severing and diverting further comprises a lip which is inclined radially inward along at least a portion of a leading edge of the aperture.

12. A catheter as in claim 6, wherein the elongated aperture is helically-disposed about a central axis of the head.

13. A catheter as in claim 12, wherein the helical aperture subtends less than a complete turn about the cylindrical cutting head.

14. A catheter as in claim 12, wherein the helical aperture subtends at least one complete turn about the cylindrical cutting head.

15. A catheter as in claim 6, further comprising means for withdrawing severed atheromatous material from the interior and through the forward distal end of the cylindrical cutting head.

16. A catheter as in claim 15, wherein the means for withdrawing severed atheromatous material comprises a spool which is slidably disposed within the interior of the cylindrical cutting head.

17. A method for removing atheromatous material from a vascular lumen comprising:
   introducing the distal end of a catheter into the vascular lumen adjacent the atheromatous material;
   rotating a cylindrical cutting head mounted at the distal end of the catheter, said head having a cylindrical wall surrounding an open interior, an axially elongated aperture in said wall, said wall having a surface area excluding said aperture which is substantially greater than the area defined by said aperture, and means for severing adjacent the aperture, whereby atheromatous material is severed and diverted into the interior of the head;
   displacing the cylindrical cutting head laterally as it is being rotated, whereby atheromatous material on the side of the catheter may be removed; and
   withdrawing the distal end of the catheter from the vascular lumen while the severed material remains captured within the walls of the cylindrical cutting head.

18. A method as in claim 17, wherein the cylindrical cutting head is rotated relative to the catheter.

19. A method as in claim 17, further comprising axially advancing the catheter within the lumen as the cylindrical cutting head is being rotated, wherein the means for severing includes a forwardly disposed cutting edge and whereby atheromatous material in front of the catheter may be removed.

20. A method as in claim 17, further comprising axially advancing the cylindrical cutting head relative to the catheter as the cutting head is being rotated, wherein the means for severing includes a forwardly disposed cutting edge and whereby atheromatous material in front of the catheter may be removed.

21. A method as in claim 17, wherein the entire catheter is rotated together with the rotating cylindrical cutting head.

22. A method as in claim 17, wherein the means for severing is shielded within a housing while the catheter is being introduced to or withdrawn from the vascular lumen.

23. A method as in claim 17, wherein the catheter is axially stationary with the vascular lumen and the means for severing includes a rearwardly disposed cutting edge, whereby the catheter experiences a distal thrust.

24. An atherectomy catheter comprising:
   a catheter body having a proximal end and a distal end;
   a housing attached to the distal end of the catheter body, said housing having a distal opening and a single axially-aligned elongated opening;
   a cylindrical cutting head rotatably mounted in the housing, said head having a cylindrical wall surrounding an open interior and an axially elongated aperture in said wall, said wall having a surface area excluding said aperture which is substantially greater than the area defined by said aperture, said head having a tapered distal end which extends through the distal opening of the housing with the aperture extending to near the tapered distal end of the head;
   means within the catheter body for rotating the cylindrical head; and
   means disposed adjacent the elongated aperture of the cylindrical head for severing atheromatous material and diverting severed material into the interior of said head as the head is rotated.

25. A catheter as in claim 24, further comprising an inflatable balloon mounted externally on the housing and disposed generally opposite the elongated opening.

26. A catheter as in claim 24, wherein the means for severing and diverting comprises a cutting edge which forms at least a portion of a trailing edge of the aperture as the cylindrical cutting head is rotated.

27. A catheter as in claim 24, wherein the means for severing and diverting further comprises a lip which is inclined radially inward along at least a portion of a leading edge of the aperture.

28. A catheter as in claim 24, wherein the elongated aperture is helically disposed about a central axis of the head.

29. A catheter as in claim 28, wherein the helical aperture subtends less than a complete turn about the cylindrical cutting head.

30. A catheter as in claim 28, wherein the helical aperture subtends least one complete turn about the cylindrical cutting head.

31. A catheter as in claim 24, further comprising means for withdrawing severed atheromatous material from the interior and through the forward distal end of the cylindrical cutting head.

32. A catheter as in claim 31, wherein the means for withdrawing severed atheromatous material comprises a spool which is slidably disposed within the interior of the cylindrical cutting head.

33. An atherectomy catheter comprising:
   a catheter body having a proximal end and a distal end;
   a housing attached to the distal end of the catheter body, said housing having a single axially-aligned elongated opening;
   a cylindrical cutting head rotatably mounted in the housing, said head having a cylindrical wall surrounding an open interior and an axially elongated helical aperture in said wall, said wall having a surface area excluding said aperture which is substantially greater than the area defined by said aperture, said aperture subtending less than a complete turn about the cylindrical cutting head;
   means within the catheter body for rotating the cylindrical head;
   means disposed adjacent the elongated aperture of the cylindrical head for severing atheromatous material and diverting severed material into the interior of said head as the head is rotated.

34. A catheter as in claim 33, further comprising an inflatable balloon mounted externally on the housing and disposed generally opposite the elongated opening.

35. A catheter as in claim 33, wherein the cylindrical cutting head is tapered at its distal end and wherein said tapered distal end extends out from an opening in the distal end of the housing.

36. A catheter as in claim 35, wherein the axially elongated aperture extends to near the tapered distal end of the head.

37. A catheter as in claim 33, wherein the means for severing and diverting comprises a cutting edge which forms at least a portion of a trailing edge of the aperture as the cylindrical cutting head is rotated.

38. A catheter as in claim 37, wherein the means for severing and diverting further comprises a lip which is inclined radially inward along at least a portion of a leading edge of the aperture.

39. A catheter as in claim 33, further comprising means for withdrawing severed atheromatous material from the interior and through the forward distal end of the cylindrical cutting head.

40. A catheter as in claim 39, wherein the means for withdrawing severed atheromatous material comprises a spool which is slidably disposed within the interior of the cylindrical cutting head.

41. A method for removing atheromatous material from a vascular lumen comprising:
introducing the distal end of a catheter into the vascular lumen adjacent the atheromatous material;
rotating a cylindrical cutting head mounted at the distal end of the catheter, said head having a cylindrical wall surrounding an open interior, an axially elongated aperture which is helically disposed in said wall and subtends less than one complete turn about the cylindrical head, said wall having a surface area excluding said aperture which is substantially greater than the area defined by said aperture, and means for severing adjacent the aperture, whereby atheromatous material is severed, diverted into the interior of the head and captured therein by said walls; and
withdrawing the distal end of the catheter from the vascular lumen while the severed material remains within the cylindrical cutting head.

42. A method as in claim 41, wherein the cylindrical cutting head is rotated relative to the catheter.

43. A method as in claim 41, further comprising axially advancing the catheter within the lumen as the cylindrical cutting head is being rotated, wherein the means for severing includes a forwardly disposed cutting edge and whereby atheromatous material in front of the catheter may be removed.

44. A method as in claim 41, further comprising axially advancing the cylindrical cutting head relative to the catheter as the cutting head is being rotated, wherein the means for severing includes a forwardly disposed cutting edge and whereby atheromatous material in front of the catheter may be removed.

45. A method as in claim 41, further comprising displacing the cylindrical cutting head laterally as it is being rotated, whereby atheromatous material on the side of the catheter may be removed.

46. A method as in claim 41, wherein the entire catheter is rotated together with the rotating cylindrical cutting head.

47. A method as in claim 41, wherein the means for severing is shielded within a housing while the catheter is being introduced to or withdrawn from the vascular lumen.

48. A method as in claim 41, wherein the catheter is axially stationary with the vascular lumen and the means for severing includes a rearwardly disposed cutting edge, whereby the catheter experiences a distal thrust.

49. A method for removing atheromatous material from a vascular lumen comprising:
introducing into the vascular lumen the distal end of a catheter comprising a housing having a single axially-aligned elongate opening at said distal end, a cylindrical cutting head mounted within the housing, said head having a cylindrical wall surrounding an open interior, an axially elongated aperture in said wall, said wall having a surface area excluding said aperture which is substantially greater than the area defined by said aperture, and means for severing adjacent the aperture, wherein the cylindrical cutting head is rotationally positioned within the housing so that the severing means is not exposed through the housing opening while the distal end is being introduced;
rotating the cylindrical cutting head after the housing has been positioned adjacent a region of atheroma, whereby atheromatous material is severed, diverted into the interior of the head and captured therein by said walls; and
withdrawing the distal end of the catheter from the vascular lumen while the severed material remains within the cylindrical cutting head.

50. A method as in claim 49, wherein the cylindrical cutting head is rotated relative to the catheter.

51. A method as in claim 49, further comprising axially advancing the catheter within the lumen as the cylindrical cutting head is being rotated, wherein the means for severing includes a forwardly disposed cutting edge and whereby atheromatous material in front of the catheter may be removed.

52. A method as in claim 49, further comprising axially advancing the cylindrical cutting head relative to the catheter as the cutting head is being rotated, wherein the means for severing includes a forwardly disposed cutting edge and whereby atheromatous material in front of the catheter may be removed.

53. A method as in claim 49, further comprising displacing the cylindrical cutting head laterally as it is being rotated, whereby atheromatous material on the side of the catheter may be removed.

54. A method as in claim 45, wherein the entire catheter is rotated together with the rotating cylindrical cutting head.

55. A method as in claim 45, wherein the catheter is axially stationary with the vascular lumen and the means for severing includes a rearwardly disposed cutting edge, whereby the catheter experiences a distal thrust.

* * * * *